United States Patent [19]

Gluckman et al.

[11] Patent Number: 5,482,926
[45] Date of Patent: Jan. 9, 1996

[54] GROWTH FACTOR IGF-IL

[75] Inventors: Peter D. Gluckman, Auckland; David J. Mellor, Palmerston North, both of New Zealand

[73] Assignee: Pharmacia AB, Sweden

[21] Appl. No.: 190,168

[22] PCT Filed: Jun. 7, 1993

[86] PCT No.: PCT/SE93/00503

§ 371 Date: Feb. 17, 1994

§ 102(e) Date: Feb. 17, 1994

[87] PCT Pub. No.: WO93/25227

PCT Pub. Date: Dec. 23, 1993

[30] Foreign Application Priority Data

Jun. 8, 1992 [NZ] New Zealand ............................ 243071

[51] Int. Cl.$^6$ ............................ A61K 38/00; C07K 13/00
[52] U.S. Cl. ............................ 514/12; 514/21; 530/303; 530/399
[58] Field of Search ........................ 514/12, 21; 530/303, 530/399

[56] References Cited

FOREIGN PATENT DOCUMENTS

| WO89/05822 | 6/1989 | WIPO . |
| WO90/15142 | 12/1990 | WIPO . |
| WO91/12018 | 8/1991 | WIPO . |
| 9200754 | 1/1992 | WIPO . |
| WO92/03155 | 3/1992 | WIPO . |

OTHER PUBLICATIONS

Heinz–Erian et al., Eudocmnology, 1991 p. 1769.
Shober et al., Endocruology, vol. 126(2), Feb. 1990, pp. 1125–1132.
Young, et al., Insulin–Like Growth Factors and the Developing and Mature Rat Small Intestine: Receptors and Biological Actions, Digestion, 1990, (46, Supplement 2), pp. 240–252.
Dialog Information Services, File 155, Medline, Dialog No. 07566682 1966–1994.
Grey, et al., Insulin–like Growth Factor II/Mannose–t–Phosphate Receptors Are Transiently Increased in the Rat Distal Intestinal Epithelium After Resection, Molecular and Cellular Endocrinology, 1991 (75), pp. 221–227.
Heinz–Erian, et al., Identification and In Situ Localization of the Insulin–Like Growth Factor–II, Endocrinology, 1991, p. 1769.
Rivard, et al., Negative Control by Sandostatin on Pancreatic and Doudenal Growth: A Possible Implication of Insulin–Like Growth Factor I, Regul–Pept., 1991, Jun. 11, vol. 34 (11), PP. 13–23 (Abstract).
Koenuma, et al., Insulin and Insulin–Like Growth Factor 1 Stimulate Proliferation of Metastatic Variants of Colon Carcinoma 26, Japan J. Cancer Res. 1989, Jan., vol. 80(1), pp. 51–58 (Abstract).
Culouscou, et al., Purification of a Colon Cancer Cell Growth Inhibitor and its Identification as an Insulin–Like Growth Factor Binding Protein, Cancer Res. 1991, Jun. 1, vol:51(11), pp. 2813–2819 (Abstract).

Primary Examiner—Jill Warden
Assistant Examiner—P. Lynn Touzeau
Attorney, Agent, or Firm—Pollock, Vande Sande & Priddy

[57] ABSTRACT

The present invention relates to the use of iGF-II or effective analogues thereof for the manufacture of a medicament for prevention or treatment of nutritional or gastrointestinal disorders and for promoting human or animal neonatal growth. It also relates to composition comprising exogenous human or animal IGF-II or effective analogues thereof in a therapeutically effective amount together with a pharmaceutically acceptable carrier or diluent or foodstuff, preferably in admixture with artificial or natural milk or colostrum. The invention may be applied both in man and in animals.

22 Claims, No Drawings

GROWTH FACTOR IGF-IL

The present invention; relates to the use of IGF-II or effective analogues thereof for the manufacture of a medicament for prevention or treatment of nutritional or gastrointestinal disorders and for promoting human or animal neonatal growth. It also relates to composition comprising exogenous human or animal IGF-II or effective analogues thereof in a therapeutically effective amount together with a pharmaceutically acceptable carrier or diluent or foodstuff, preferably in admixture with artificial or natural milk or colostrum. The invention may be applied both in man and in animals.

INTRODUCTION AND PRIOR ART

Insulin-like growth factor 2 (IGF-II) is a peptide present in plasma and other body fluids. Its primary sequences shows 64% homology to IGF-I and comprises 67 amino acids, including 3 disulphide bonds. It can stimulate growth of a wide range of cell types. IGF-II have been purified from human plasma and the complete amino acid sequence is known. Sequences with extensive homologies to human IGF-II are present in IGF-II purified from plasma of other species. IGF-II has systemic and local effects and appear mostly associated with different specific binding problems, six of which are sequenced and are termed IGFBP1, IGFBP2, IGFBF3, IGFBP4, IGFBP5 and IGFBP6. These appear to modulate the biological functions and availability of IGF-II in both a positive and negative manner. IGF-II appears to act mainly by interactions with the IGF-type 1 receptor exposed on the outer surface of plasma membranes in many different cell types—however relative specificity of action rosy be found because of the influence of binding proteins. IGF-II may also have distinct actions as it binds to a distinct and unrelated type 2 receptor also found on cell membranes. Moreover, binding of IGF-II to insulin receptors also seems to be of importance. Because of the scarcity of purified plasma IGF-II there was a great necessity to develop methodology for the commercial scale production of IGF-II. Nowadays such large scale production can readily be achieved by using recombinant DNA techniques. IGF-II has been shown to experimentally reduce the catabolic state in starved animals and to antagonise some metabolic actions of IGF-I (Koea et al Endocrinology 1992, 130, 2423–2425). These observations of Koea et al plus the different range of receptor specificities of IGF-II to that of IGF-I mean that there is no obviousness to any action of IGF-II on the gastrointestinal tract.

It has previously been demonstrated that both type I and type 2 IGF receptors are present in the gastrointestinal tract and that oral IGF-I and IGF-II affect jejunal enzymes following repeated administration in older suckling rats, but no effect on intestinal growth was observed. (Young et al. Digestion 46, (1990), Suppl. 2, 240–252). Ballard et al , WO 91/12018 have disclosed the therapeutic use of IGF-I for gastrointestinal disease or the treatment of the shortened gut after surgery. Ballard provide no evidence of activity following oral administration.

Heinze-Erian et al, Endocrinology, (1991) Vol 129, No 4, 1769, reports that there is an essential role for both IGF receptors in the regulation of cell mitogenesis and growth.

Grey Vet al, Mol-Cell-Endocrinol, 1991, Mar, Vol 75 (3), 221–7 suggests that IGF-II/man-6-P receptor may play a role in the adaptive regenerative response of the intestinal epithelium.

There was however not a priori reason to believe that IGF-II might be efficacious in the normal gut in the premature or immediately neonatal gut and the prior art does not demonstrate any known action of IGF-II on the gastrointestinal system.

No studies of the effects of oral administration of the IGF-II on the neonatal gastrointestinal system, nutritional status or growth have been previously suggested.

There is a need for a medicament for prevention or treatment of nutritional or gastrointestinal disorders.

It has now surprisingly been found that IGF-II or effective analogues thereof can be used for the manufacture of such a medicament which also can be used for promoting human or animal neonatal growth.

THE INVENTION

The invention relates to the use of IGF-II or effective analogues thereof for the manufacture of a medicament for prevention or treatment of nutritional or gastrointestinal disorders and for promoting human or animal neonatal growth.

The medicament promotes e.g. intestinal mucosal growth and cell proliferation, intestinal and gastointestinal muscle growth following surgery or in disorders of the gastrointestinal tract.

The medicament can restore or maintain gastrointestinal function after periods of parenteral nutrition or after gastrointestinal disease including gastroenteritis, inflammatory bowel disease, bowel surgery ulceration of the duodenum or to accelerate recovery.

The medicament also promotes villous growth and enhances nutritional status in patients with mucosal villous diseases such as coeliac disease, post infective villous atrophy and short gut syndromes.

Another aspects of the invention is the use in which the medicament promotes growth of neonatal and premature human or animal, such as growth of premature infants, reduces the risk of necrotising enterocolitis and reduces the risk of infection of the gastrointestinal tract.

The medicament promotes villous growth and enhance nutritional status in premature infants or in growth retarded infants and reduces the risk of enteric disease such as enteritis in the neonate.

Human or animal IGF-I can be used and may be given singly or in combination with other growth factors such as IGF-I and epidermal growth factor (EGF) for enhancing or improving the desired effect(s) of IGF-II or its effective analogues.

The invention also relates to a composition comprising human or animal IGF-II or effective analogues thereof in a therapeutical effective amount together with a pharmaceutically acceptable carrier or diluent, preferably adapted for oral, gastric or interna; administration and most preferably together with milk or colostrum.

This composition is intended for promoting growth, thrift or nutrition in man or animals or for reducing the risk of intestinal infection.

A Regarding the use for prevention or treatment of nutritional or gastrointestinal disorders, the following uses are pointed out:
I In man:
 1) Promotion of villous growth in older subjects In diseases associated with villous atrophy, flattening or where there is malabsorption including coeliac disease, cystic fibrosis, inflammatory diseases of the bowel (e.g. Crohns disease), following gastroenteritis, following intestinal surgery including resection.

2) Treatment of inflammatory diseases of the bowel (e.g. Crohns disease).
3) Treatment of post-inflammatory villous atrophy.
4) Treatment of malabsorption disorders.
5) Treatment of short gut syndromes.
6) Acceleration of gut recovery following bacterial, viral or amoebic enteritis or giardiasis.
7) Prophylaxis against necrotising enterocolitis.
8) Maintenance of gastrointestinal function in parenterally fed subjects, particularly neonates.
9) Acceleration of growth in growth retarded infants.

II In animals:
1) Prophylaxis or treatment of inflammatory conditions of the gastrointestinal tract particularly in infancy.
2) Promotion of infant growth by supplementation of artificial or natural milks fed to infant animals.
3) Treatment of gastrointestinal disorders or disturbances at weaning.
4) Promotion of growth of the smooth muscle layer of the intestine. In situations such as following intestinal surgery full gastronutritional function may be recovered more quickly if muscular growth is enhanced.

In primary constipation, or secondary to disorders of neural innervation of the gastrointestinal system increased muscle mass may be of value.

In animal either recombinant human IGF-II or IGF-II of other species (e.g. bovine, porcine) may be used either as an oral drench or as a supplement to artificial liquid or solid feeds.

B. Regarding the use for promoting human or animal neonatal growth the following uses are pointed out, but are not limited to:

1) Promotion of intestinal mucosal cell proliferation and villous growth and/or crypt depth in the neonate.

The property of IGF-II or its effective analogues when administered orally in the neonate is useful for the prevention treatment of a variety of primary or secondary neonatal nutritional and gastrointestinal disorders and in improving the management of the neonate.

2) Promotion of growth, gut and pancreatic development in growth retarded newborns.
3) Acceleration of the initiation of oral feeding in premature infants.
4) Reducing the risk of necrotising enterocolitis in the premature infant.
5) Improving nutritional status in the growth retarded infant.
6) Preservation of gastrointestinal function and growth in infants deprived of oral feeding for prolonged periods (for example extreme prematurity or following gastrointestinal surgery) or acceleration of switching from parentoral to oral feeding in such infants.
7) As a supplement to the management of the neonates, infants or children with deficient growth or health associated with impaired oral nutrition for example following gastrointestinal infection or associated with specific disease of the gastointestinal tract such as following necrotising enterocolitis, following gastrointestinal surgery or with primary or secondary villous atrophy.
8) Acceleration of normal infant growth in animal.

Preferably in man human IGF-II singly or in combination with IGF-I is used. The dose given could be 0.01 to 100 µg/kg/body weight per day. The preferred route of administration is by mouth either in aqueous buffer or other pharmacological composition or added to artificial feed, artificial or natural milk. Alternatively it may be installed more distally in the gastrointestinal tract for example by nasogastric tube or by duodenal tube.

C Pharmaceutical composition comprising IGF-II.

The present invention in respect of all the above provides a pharmaceutical composition that includes an effective amount of a peptide or effective analogue of IGF-II and a pharmaceutically acceptable carrier or diluent, preferably adapted for oral, gastric, or internal administration. The peptide may be present in amounts sufficient to provide a dose rate of approximately 0.01 to 100 µg/kg body weight per day, preferably 0.1–10 µg/kg per day.

D. The claimed composition can be used as a supplement to foodstuff,

The foodstuff is preferably milk to promote nutrition, growth and reduce the impact of gastrointestinal infection. It is desirable in human infants with growth failure, prematurity of where there is difficulty in establishing oral feeding. The use is particularly desirable in infant animals from large litters, on artificial feeds or where there is growth retardation present. The invention also extends to a nutritionally acceptable composition for the supplementation of natural or artificial milk formula for human or animal use such that IGF-II or analogue is provided. The peptide may be present in amounts sufficient to provide a dose rate of approximately 0.01 to 100 µg/kg body weight per day, preferably 0.1–10 µg/kg per day.

DETAILED DESCRIPTION OF THE INVENTION

The preferred form of the invention will now be described with reference to the following non-limiting example.

EXAMPLE 1

Studies were performed in newborn piglets that were raised for 24 hours following birth with a commercial infant milk formula (SMA Gold Cap; John Wyeth & Bro (NZ) Ltd) containing undetectable (<1 ng/ml) levels of IGF-I or IGF-II or with the same formula supplemented with either 2 µg/ml of recombinant human IGF-I or recombinant human IGF-II (provided by Kabi Pharmacia AB, Sweden). 7 piglets received each treatment. The piglets were from 7 litters and each litter provided on one formula fed and one formula plus IGF-II fed piglet. The piglets had statistically similar birth weights. After birth the piglets were fed by bottle 20 ml/kg every 2 hours for the first 12 hours, then 40 ml/kg every 4 hours thereafter until slaughter. The animals were slaughtered at 24 hours after birth for histological evaluation.

In addition the rate of cell proliferation was assessed by administering bromodoxyuridine (BRDU) intraperitoneally to the piglet in 4 equal doses of 5 mg/kg at 30 minute intervals between 120 and 30 mins prior to slaughter. BRDU labelling can be detected histologically and indicates active cell proliferation. The net weights of the cleaned gastrointestinal tract components were compared (see Tables 1 to 3). Tissue blocks were taken from the mid duodenum, the proximal and distal jejunum and the proximal and distal ileum and histological measurements were made using images projected onto a digitizer pad and quantified by computer programme (Sigma Scan). Further analysis for RNA, DNA and protein content were performed on proximal jejunal mucosa (Table 4).

TABLE 1

Mean body-weight and weights and physical dimensions of digestive organs in 24 hour old piglets raised on an infant formula with or without addition of IGF-II.

|  | Treatment | |
|---|---|---|
|  | Control n = 7 | IGF-II n = 7 |
| Birth Weight (kg) | 1.286 | 1.295 |
| Final Weight (kg) | 1.318 | 1.320 |
| Stomach weight (g/kg)# | 5.02 | 4.99 |
| Pancreas weight (g/kg)# | 1.23 | 1.37* |
| Small intestine: | | |
| Weight (g/kg)# | 29 | 29 |
| Length (cm/kg)# | 310 | 323 |
| Mitotic index (cells/crypt labelled) | 6.93 | 8.63*** |
| Large intestine: | | |
| Weight (g/kg)# | 6.2 | 6.4 |
| Length (cm/kg)# | 69 | 72 |

Adjusted for the birth weight.
*$p < 0.05$?
***$p < 0.001$

TABLE 2

Effects of oral ingestion of IGF-II on the mean weights of small intestinal mucosal and muscle (n = 5/group).

|  | Control (g) | % difference from control IGF-II |
|---|---|---|
| Duodenal mucosa | 0.54 | 15.6 |
| Duodenal muscle | 0.44 | 19.4 |
| Jejunal mucosa | 9.90 | 30.2 |
| Jejunal muscle | 3.27 | 18.7 |
| Ileal mucosa | 7.82 | 29.2 |
| Ileal muscle | 3.15 | 36.3 |

TABLE 3

Mean microscopic measurements (μm) and mean cell proliferation rate in the small intestine of 24 hour old piglets raised on an infant formula with or without addition of IGF-II (n = 5/group).

|  | Control | IGF-II |
|---|---|---|
| Wall thickness | 1019 | 1100 |
| Villus length | 725 | 784 |
| Crypt depth | 97 | 106 |
| Submucosa thickness | 93 | 94 |
| Muscularis thickness | 79 | 88 |

TABLE 4

Chemical compositions of the proximal jejunal mucosa. (n = 5/group)

|  | Control | IGF-II |
|---|---|---|
| Weight (g/kg)# | 5.712 | 6.147 |
| Protein (mg/kg)# | 583 | 559 |
| RNA (mg/kg)# | 28.9 | 31.0 |
| DNA (mg/kg)# | 25.0 | 28.1 |
| Protein: DNA | 23.0 | 20.0 |
| RNA: DNA ratio (mg/mg) | 1.14 | 1.11 |

Adjusted for the birth weight.

These observations provide clear evidence that in neonatal animals oral administration of IGF-I is selectively active to promote mitosis of crypt cells in the small intestine. These cells are the source of the enterocytes that form the absorptive layer on the intestinal villous. It will also promote intestinal growth of the villous mucosa and promote muscle growth.

Finally it has to be understood that various other modifications and/or alterations may be made without departing from the spirit of the present invention as outlined therein.

We claim:

1. Composition for the treatment of nutritional or gastrointestinal disorders or for promoting human or animal neonatal growth comprising human or animal IGF-II in a therapeutical effective amount together with a pharmaceutically acceptable carrier or diluent, wherein said carrier or diluent is for oral or gastric administration and wherein said carrier or diluent comprises natural milk or colorstrum.

2. The composition of claim 1 Wherein said carrier or diluent is for oral administration.

3. Composition according to claim 1 for promoting growth, thrift or nutrition in man or animals or reducing the risk of intestinal infection.

4. The method for the treatment of nutritional or gastrointestinal disorders or for promoting human or animal neonatal growth in a patient in need thereof which comprises administering to said patient a medicament for oral or gastric administration and wherein said carrier or diluent comprises natural milk or colostrum comprising a therapeutically effective amount of IGF-II.

5. The method of claim 4 wherein said IGF-II is human IGF-II.

6. The method of claim 4 wherein said IGF-II is animal IGF-II.

7. The method of claim 4 wherein said medicament is administered orally.

8. The method of claim 4 for promoting intestinal mucosal growth.

9. The method of claim 4 for promoting gastrointestinal muscle growth following surgery or in disorders of the gastrointestinal tract.

10. The method of claim 4 for restoring or maintaining gastrointestinal function after periods of parenteral nutrition or after gastrointestinal disease or to accelerate recovery.

11. The method of claim 4 for promoting villus growth and enhances nutritional status in patients with mucosal villous diseases.

12. The method of claim 4 for promoting growth of neonatal and premature human or animal.

13. The method of claim 12 for promoting growth and development of neonatal animals, growth of premature infants and reducing the risk of necrotizing enterocolitis and infection of gastrointestinal tract.

14. The method of claim 12 for promoting villous growth and enhanced nutritional status in premature infants or in growth retarded infants.

15. The method of claim 12 for reducing the risk of enteric disease.

16. The method of claim 10 wherein said disease is selected from the group consisting of gastroenteritis, inflammatory bowel disease, and bowel surgery ulceration of the duodenum.

17. The method of claim 11 wherein said mucosal villous diseases are selected from the group consisting of coeliac disease, past infective villous atrophy and short gut syndromes.

18. The method of claim 12 for reducing the risk of enteritis in a neonate.

19. The method of claim 4 wherein said patient is a neonate.

20. The method of claim 4 wherein said patient is a premature infant.

21. The composition of claim 1 which consists of said IGF-II as the active ingredient.

22. The method of claim 4 which consists of administering said IGF-II as the active ingredient.

* * * * *